United States Patent [19]

Brundbjerg

[11] 4,203,948

[45] May 20, 1980

[54] AIR PURIFIER OF THE REGENERATING TYPE

[76] Inventor: Niels Brundbjerg, Resedavej 12, DK-2820 Gentofte, Denmark

[21] Appl. No.: 928,160

[22] Filed: Jul. 26, 1978

[30] Foreign Application Priority Data

Aug. 4, 1977 [DK] Denmark .............................. 3499/77

[51] Int. Cl.² ........................... B03C 3/43; B03C 3/82
[52] U.S. Cl. ..................................... 422/121; 55/102; 55/136; 55/279; 422/240
[58] Field of Search ................ 55/102, 136, 138, 279; 422/4, 30, 120, 121, 123, 240, 186; 250/432 R, 435, 455; 204/193

[56] References Cited

U.S. PATENT DOCUMENTS

| 2,449,681 | 9/1948 | Wilson | 55/102 |
| 2,489,786 | 11/1949 | Klemperer | 55/138 |
| 2,490,979 | 12/1949 | Palmer | 55/136 |
| 2,980,202 | 4/1961 | Meyer | 55/102 |
| 3,072,978 | 1/1963 | Minto | 55/279 |
| 3,937,967 | 2/1976 | Steinitz | 55/102 |
| 4,102,654 | 7/1978 | Pellin | 55/102 |

FOREIGN PATENT DOCUMENTS 931625 7/1963 United Kingdom ..................... 55/102

Primary Examiner—David L. Lacey
Attorney, Agent, or Firm—Cushman, Darby & Cushman

[57] ABSTRACT

The invention relates to an air purifier comprising a mercury lamp emitting electrons and generating ozone during the purification. The air purifier is surrounded by a non-conductive casing absorbing molecules negatively charged due to the emitted electrons. As a result the ozone molecules become positively charged and may therefore recombine with negatively charged ozone molecules to produce neutral oxygen molecules.

3 Claims, 2 Drawing Figures

U.S. Patent  May 20, 1980  4,203,948

AIR PURIFIER OF THE REGENERATING TYPE

The invention relates to an air purifier of the regenerating type and comprising radiating means such as a mercury lamp, and wherein the air is flowing through an electric field in an electron-cloud forming member.

It is known to sterilize air by passing the air through an electrostatic field. As a result ozone is, however, produced, cf. e.g. the German specifications Nos. 2,452,824 and 2,205,885.

$O_3$ can furthermore be reduced to $O_2$ by oxidizing a metallic material, cf. British patent specification No. 1,400,519. This filter method is, however, not particularly efficient. Furthermore, the filter material must be replaced from time to time.

The object of the invention is to provide an air purifier able to sterilize air and neutralize the ozone molecules in a more efficient manner.

The air purifier according to the invention is characterized by the radiating means being surrounded by a charge absorbing, nonconductive casing. As a result the ozone molecules become positively charged, whereby a reaction and thereby a neutralization with negatively charged ozone molecules is facilitated.

According to a preferred embodiment of the invention the nonconductive casing is made of a, for example, soft, plumbiferous plastic.

Figure 1:
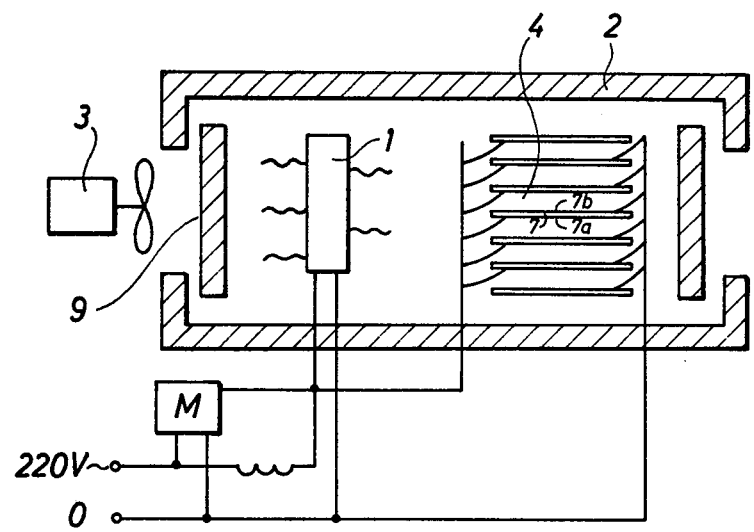
Figure 2:
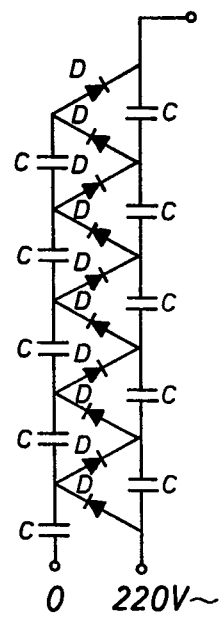

The invention will be described below with reference to the accompanying drawing, in which FIG. 1 illustrates the air purifier according to the invention, and FIG. 2 illustrates a voltage multiplier forming part of the air purifier.

The air purifier according to the invention operates in accordance with the regeneration principle. It comprises a radiating means 1 such as a mercury lamp emitting both electrons and X-rays. By applying a voltage of 220 VAC, the X-ray wave length is in the range of 300–400 nm. By applying a voltage of 8000 V, the wave length range is increased to about 165 nm. At a wave length of 210 nm a destruction of DNA molecules and thereby a destruction of germ and virus takes place. At a wave length of 250 nm a cell division takes place, said cell division being so fast that the cells produced cannot survive. By the electron bombardment the oxygen, hydrogen, and nitrogen bound to heavy molecules such as sulphur, chlorine or metals, are liberated. The heavy molecules are detected and received by the material of the chamber, while the liberated oxygen molecules produce ozone molecules. These ozone molecules are, however, positively charged due to the fact that the heavy particles detected and captured by the chamber material are negatively charged (the chamber material should be nonconductive). An electron-cloud forming member, preferably a capacitor-like member 4, is placed behind the radiating means 1, said member generating negatively charged $O_3$ molecules. When a positively charged $O_3$ molecule meets a negatively charged $O_3$ molecule, the oppositely charged molecules recombine to produce $O_2$ molecules.

The voltage drop above the capacitor-like member 4 is for instance of the magnitude 8000 V, which substantially corresponds to the voltage necessary for the radiating means 1 to emit X-rays having wave lengths down to 165 nm.

A voltage multiplier M constructed as shown in FIG. 2 comprises a sufficient number of capacitors C mutually connected through rectifier diodes in such manner that the charge can only be transmitted in one direction. FIG. 2 shows only 10 capacitors.

The capacitor-like member 4 is composed of circuit carts 7 having metal coatings 7a and 7b on both sides. The surfaces of these coatings are suited for emission of electrons. The number of plates 7 may be varied. The surface area of each plate is of the magnitude $10 \times 10$ cm$^2$. The mutual distance between the plates is for instance of the magnitude 1 cm. The casing 2 surrounding the radiating means 1 and the capacitor-like member 4 is composed of a, for example, soft, plumbiferous plastic. A separate plumbiferous coating may also be provided on the outside of the casing 2. A blower 3 is situated at an inlet opening 9, which is constructed in such manner that radiation from 1 cannot escape.

An air purifier with a power consumption of 80 W can treat 60 m$^3$ air per hour.

A choke coil is inserted between the output of the voltage multiplier M and the phase terminal.

The power supplied at the high voltage is relatively low. Furthermore, a DC-discharge from the multiplier only occurs at every half wave of the voltage.

The air purifier according to the invention is inexpensive to produce. The most expensive portion is the casing.

By using the air purifier according to the invention the oxygen content in a room is increased by less than 6–8%.

The air purifier, which may be varied in many ways without deviating from the scope of the invention, is mainly intended for aircrafts, automobiles or hospitals. The purifier may, however, also be industrially used or in offices. When industrially used, the air purifier improves the air for the employees. It is easy to mount, since it does not require ventilating ducts. Furthermore, no thermal loss occurs. In bacon factories it increases the keeping qualities of the meat since only virus and bacteria are killed.

I claim:

1. An air purifier comprising a housing constructed of a negative charge absorbing non-conductive material, said housing having an air inlet and an air outlet; means for flowing an air stream through said housing from said inlet to said outlet; radiating means in said housing for emitting electrons and X-rays having a wavelength of at least 165 nm and producing in the stream ozone molecules which become positively charged due to the housing absorbing negatively charged particles; electron-cloud forming means having an electric field and arranged within said housing downstream of the radiating means for generating in the stream, as the latter flows through the electric field, ozone molecules which are negatively charged whereby the positively charged and negatively charged ozone molecules react to produce oxygen so as to reduce the ozone content of the stream leaving the outlet.

2. An air purifier as in claim 1 wherein said radiating means is a mercury lamp for emitting electrons and X-rays.

3. An air purifier as in claim 1 wherein the material of the housing is plumbiferous plastic.

* * * * *